US00PP23199P3

(12) United States Plant Patent
Perl et al.

(10) Patent No.: US PP23,199 P3
(45) Date of Patent: Nov. 20, 2012

(54) GRAPEVINE NAMED 'GREEN ONYX'

(50) Latin Name: ***Vitis vinifera* L.**
Varietal Denomination: GREEN ONYX

(75) Inventors: Avichai Perl, Rishon Lezion (IL); Nachman Sahar, Rehovot (IL); Oded Degani, Moshav sde Moshe (IL); Tatiana Okun, Rehovot (IL); Arie Sarfian, Nes-Ziona (IL); Hanan Bazak, Carmei Yossef (IL); Refael Eliassi, Neve Yamin (IL); Ahuva Daos, Ganey Hmoshava Mazkeret Batia (IL)

(73) Assignee: State of Israel, Ministry of Agriculture & Rural Development, Agricultural Research Organazation, Bet Dagan (IL)

( * ) Notice: Subject to any disclaimer, the term of this patent is extended or adjusted under 35 U.S.C. 154(b) by 0 days.

(21) Appl. No.: 12/929,129

(22) Filed: Jan. 3, 2011

(65) Prior Publication Data

US 2011/0277197 P1 Nov. 10, 2011

(30) Foreign Application Priority Data

Jan. 4, 2010 (IL) ..... 4236

(51) Int. Cl.
*A01H 5/00* (2006.01)

(52) U.S. Cl. ..... Plt./206

(58) Field of Classification Search ..... Plt./207
See application file for complete search history.

*Primary Examiner* — Annette Para
(74) *Attorney, Agent, or Firm* — Foley & Lardner LLP

(57) ABSTRACT

This invention relates to a new and distinct variety of grapevine named 'GREEN ANGELS'. The new early ripening, very fertile grapevine variety is particularly characterized by an attractive berry color, a very uniform bunch and a firm berry with tender crunchy skin.

5 Drawing Sheets

Botanical name of the genus and species of the plant claimed: *Vitis vinifera* L.

Variety denomination: 'GREEN ANGELS'.

PRIORITY CLAIM

This application claims priority under 35 U.S.C. §119(f) of the Israeli Plant Breeders' Rights Application No. 4236 filed Jan. 4, 2010.

BACKGROUND OF THE INVENTION

The present invention relates to a new and distinct grapevine variety, botanically known as *Vitis vinifera* L., and hereinafter referred to by its variety denomination 'GREEN ANGELS'.

The new grapevine 'GREEN ANGELS' is a product of a controlled breeding program conducted by the inventors, Avichai Perl, Nachman Sahar, Oded Degani, Tatiana Okun, Arie Sarfian, Hanan Bazak, Refael Eliassi and Ahuva Daos at The Volcani Center, located in Bet Dagan, Israel. The objective of the breeding program was to develop a new early ripening, very fertile grapevine variety particularly characterized by attractive berries with yellowish green color which are uniform in size and shape and are firm with tender crunchy skin.

The new grapevine 'GREEN ANGELS' originated from a cross made by the inventors in 2004 at The Volcani Center. The female or seed parent is the grapevine *Vitis vinifera* L indicated as 'ARO 2117' (unpatented), in the inventors' collection located in Bet Dagan, Israel, and the male or pollen parent is the grapevine *Vitis vinifera* L. indicated as 'ARO 1717' (unpatented), in the inventors' collection.

The new grapevine 'GREEN ANGELS' was observed and selected by the inventors within the progeny of the stated cross in a controlled environment in 2007 at The Volcani Center. Asexual propagation of the new grapevine variety by bud grafting was first performed in January 2008 at The Volcani Center, and has demonstrated that the combination of characteristics as herein disclosed for the new variety is firmly fixed and retained through successive generations of asexual propagation. The new cultivar propagates true-to-type.

SUMMARY OF THE INVENTION

'GREEN ANGELS' can be grown in various climates and growing conditions. The variety produces and maintains a strong vigorous plant and consistent fruit production from end June through end July in Bet Dagan, Israel.

The following traits have been repeatedly observed and are determined to be characteristics of 'GREEN ANGELS', which in combination distinguish this grapevine as a new, unique and distinct variety.

1. Very fertile;
2. Early ripening;
3. Firm berry with tender crunchy skin;
4. Attractive yellow green berry color; and
5. Berries which are uniform in size and shape.

Plants of the new grapevine 'GREEN ANGELS' differ from plants of the parents, *Vitis vinifera* L. 'ARO 2117' (unpatented) and *Vitis vinifera* L. 'ARO 1717' (unpatented), in the following characteristics described in Table 1.

TABLE 1

Comparison with parent varieties.

| Characteristic | New Variety 'GREEN ANGELS' | Female Parent 'ARO 2117' (unpatented) | Male Parent 'ARO 1717' (unpatented) |
|---|---|---|---|
| Berry shape | elongated-elliptic | rounded | elongated |
| Berry color of skin | yellowish green | yellow green | yellow green |
| Berry thickness of skin | medium | very thick | medium |
| Seeds | absent | absent | absent |

Of the many commercial varieties known to the present inventors, the most similar to the new grapevine 'GREEN ANGELS' are *Vitis vinifera* L. 'SUGRAONE' (U.S. Plant Pat. No. 3,106) and *Vitis vinifera* L. 'PRIME' (registered for Israeli Plant Breeders' Rights No. 1467), which differ from the new grapevine 'GREEN ANGELS' in the characteristics described in Table 2:

TABLE 2

Comparison with similar varieties.

| Characteristic | New Variety 'GREEN ANGELS' | Comparison Variety 'SUGRAONE' (patented) | Comparison Variety 'PRIME' ( registered) |
|---|---|---|---|
| Berry shape | elongated-elliptic | obtuse ovate | oblong |
| Berry color of skin | yellowish green | yellow green | yellow green |
| Berry thickness of skin | medium | medium | medium |
| Seeds | absent | absent | absent |

BRIEF DESCRIPTION OF THE PHOTOGRAPHS

The accompanying photographs illustrate the overall appearance of the new grapevine 'GREEN ANGELS' showing the colors as true as is reasonably possible with colored reproductions of this type. Colors in the photographs may differ slightly from the color values cited in the detailed morphological description, which accurately describe the color of 'GREEN ANGELS'.

DETAILED MORPHOLOGICAL DESCRIPTION

Figure 1:
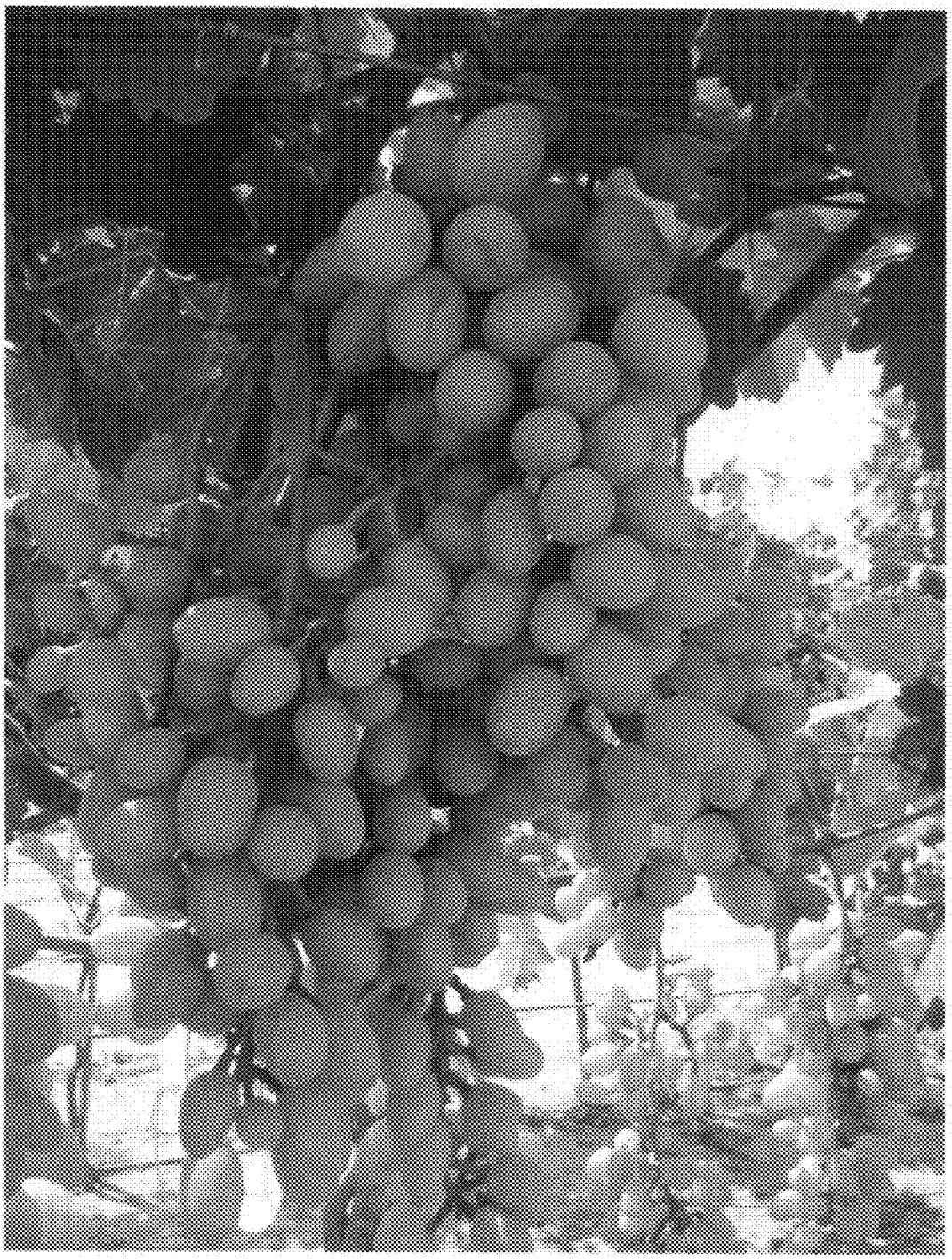
FIG. 1 shows a typical bunch of 'GREEN ANGELS' on the plant.
Figure 2:
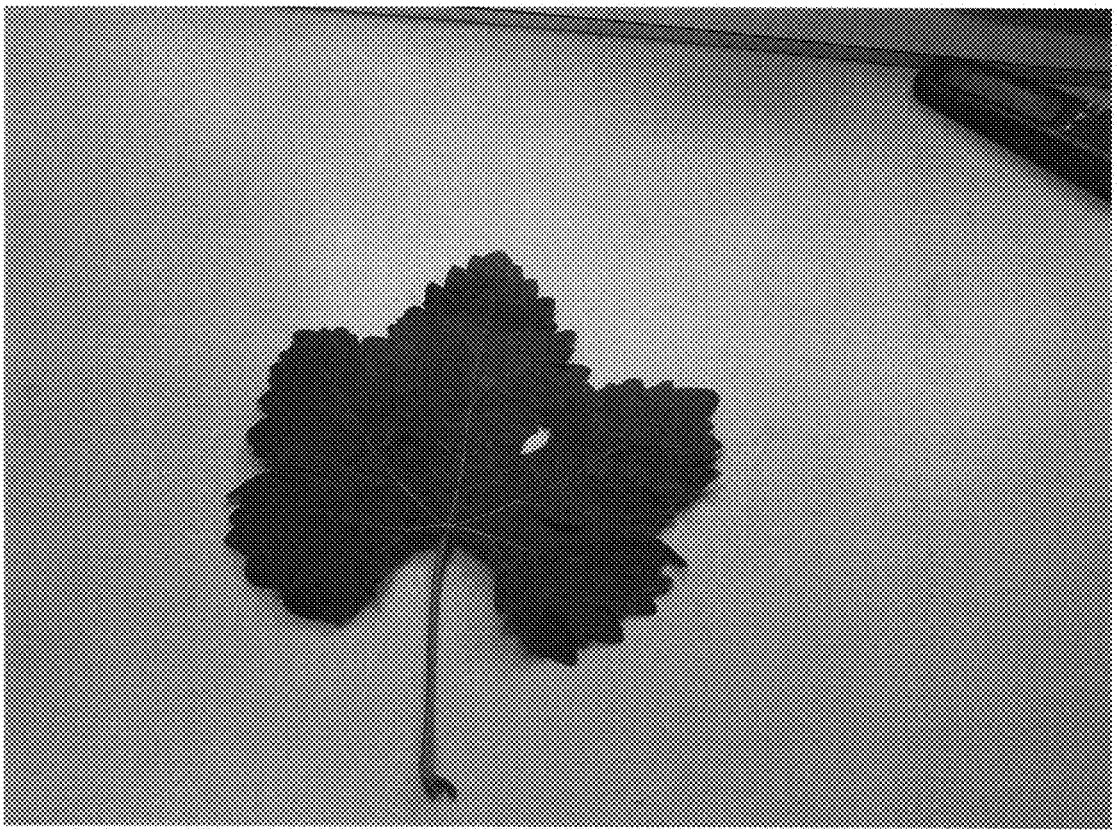
FIG. 2 shows a typical mature leaf of 'GREEN ANGELS'.
Figure 3:
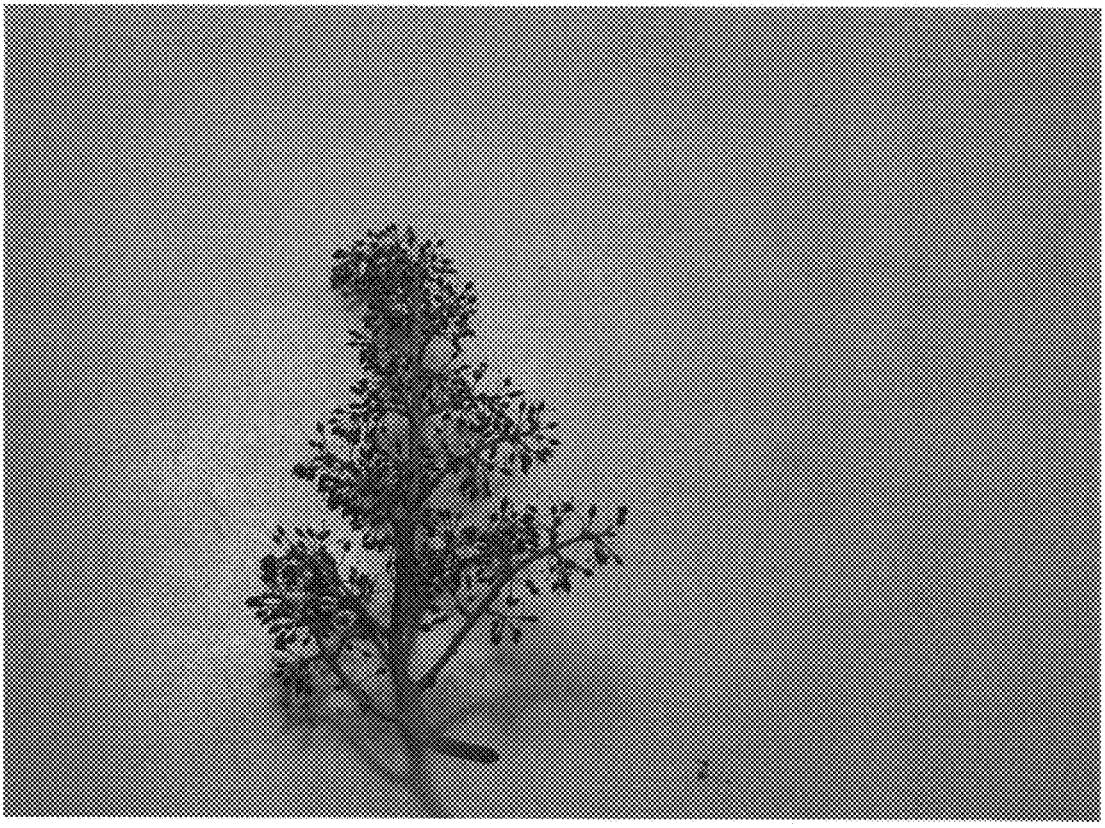
FIG. 3 shows a typical inflorescence of 'GREEN ANGELS'.
Figure 4:
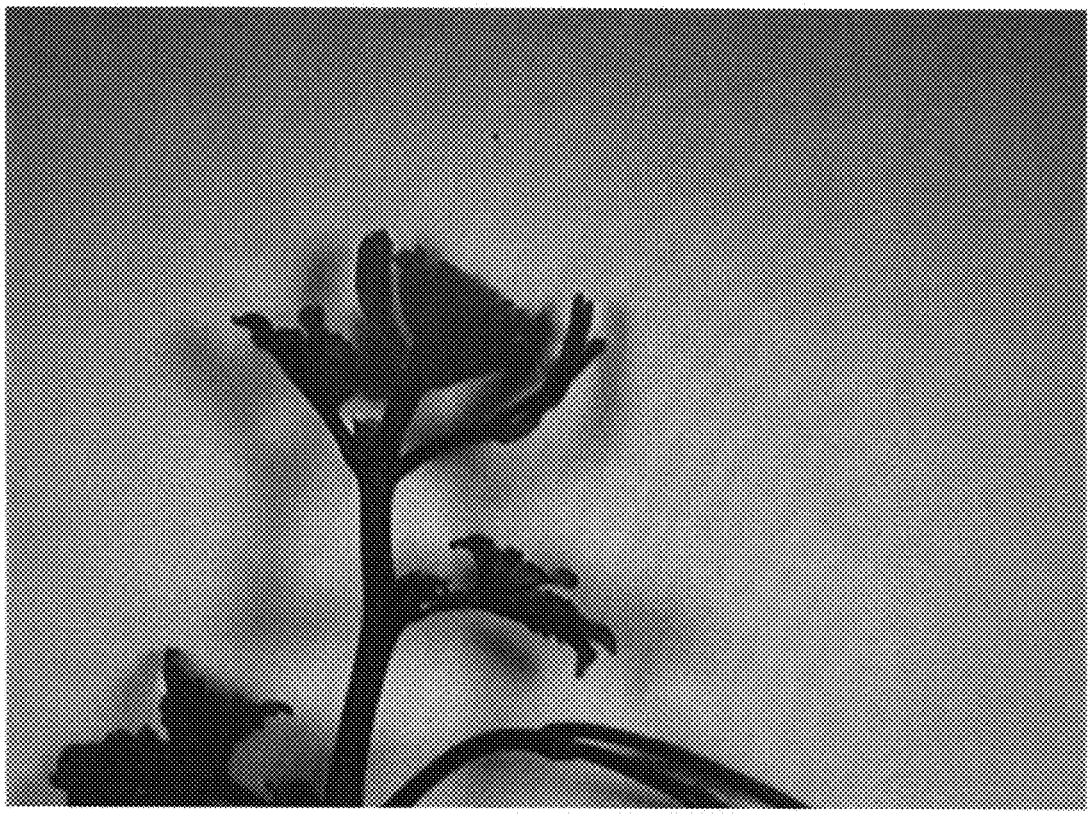
FIG. 4 shows a typical growth tip of 'GREEN ANGELS'.
Figure 5:
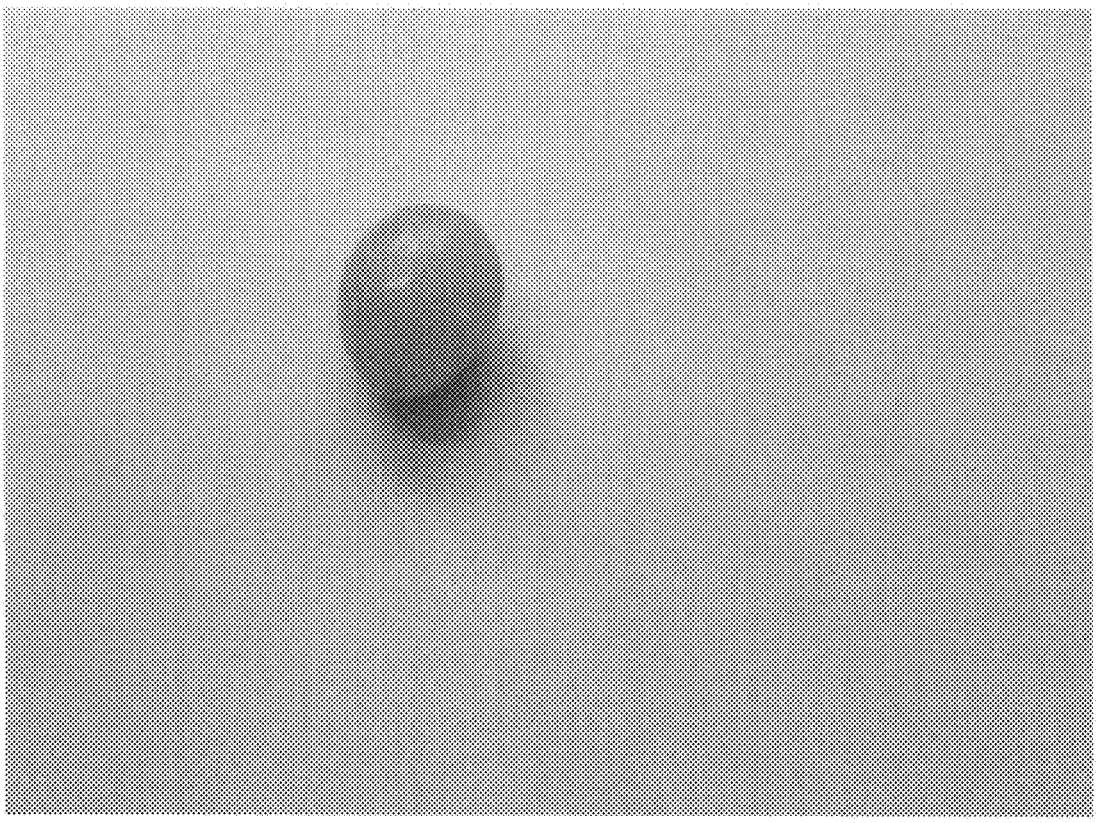
FIG. 5 shows a typical berry of 'GREEN ANGELS'.

The new *Vitis vinifera* L. 'GREEN ANGELS' has not been observed under all possible environmental conditions. The phenotypical descriptions and color designations stated for the new variety may vary, depending on variations in environmental factors, including weather (temperature, humidity and light intensity), day length, soil type, location and cultural conditions, without any change in the genotype of the grapevine.

The following description of 'GREEN ANGELS' unless otherwise noted, is based on observations and measurements taken during 2010 and 2011 at The Volcani Center, on plants grown in the vineyard located in Bet Dagan, Israel under conditions which closely approximate those generally used in commercial practice. The described plants were grafted on 'Richter110' (unpatented) and planted at a distance of 1.5 m in sandy red loam soil at an elevation of about 30 meters above sea level with drip-irrigation up to 40 $m^3$ per hectare in the peak season in the summer and Shefer 737+micro-elements 1.5 ltr. fertilizers in each 5 $m^3$ of water. Average annual rainfall is about 550 mm, with an average of 350 mm rainfall in winter (December through February). Mean diurnal minimum temperature in January is 7.2° C., and mean diurnal maximum temperature in July is 30.8° C.

Unless otherwise stated, the detailed morphological description includes observations, measurements and values based on three-year-old 'GREEN ANGELS' plants grown in the vineyard at The Volcani Center, located in Bet Dagan, Israel from 2010 to 2011. Quantified measurements are expressed as an average of measurements taken from a number of plants of 'GREEN ANGELS'. The measurements of any individual plant, or any group of plants, of the new variety may vary from the stated average.

Color references are made to The Royal Horticultural Society Colour Chart (R.H.S.), 1986 edition, except where general colors of ordinary significance are used. Color values were taken under daylight conditions in full sunlight in Bet Dagan, Israel.

All of the plants of 'GREEN ANGELS', insofar as they have been observed, have been consistent in all the characteristics described below.

Classification:

*Botanical.*—*Vitis vinifera* L.

Parentage:

*Female or Seed Parent.*—*Vitis vinifera* L. 'ARO 2117' (unpatented).

*Male or Pollen Parent.*—*Vitis vinifera* L. 'ARO 1717' (unpatented).

Propagation: Grafting onto 'Richter110' (unpatented), Interspecific Cross, *V. berlandieri* Planch×*V. rupestris* Scheele.

Growing conditions:

*Light intensities.*—Full sunlight.

*Temperature.*—Bet Dagan.—30 meters above sea level.

| | January | February | March | April |
|---|---|---|---|---|
| Mean maximum air temperature (° C.) | 17.8 | 18.1 | 20.1 | 24.5 |
| Mean minimum air temperature (° C.) | 7.2 | 7.1 | 8.8 | 11.5 |
| Mean rainfall (mm) | 140.5 | 96.9 | 66.1 | 17.5 |
| | May | June | July | August |
| Mean maximum air temperature (° C.) | 27 | 29.2 | 30.8 | 31.2 |
| Mean minimum air temperature (° C.) | 14.6 | 17.9 | 20.6 | 21.2 |
| Mean rainfall (mm) | 2.2 | — | — | — |
| | September | October | November | December |
| Mean maximum air temperature (° C.) | 30.4 | 28.3 | 24.1 | 19.7 |
| Mean minimum air temperature (° C.) | 19.4 | 16 | 11.8 | 8.6 |
| Mean rainfall (mm) | 0.4 | 20.4 | 76.2 | 130.3 |

*Fertilization.*—A balanced fertilizer with level of Shefer 737+microelements 1.5 ltr. in each 5 $m^3$ of water.

*Growth regulators.*—None applied.

*Pruning.*—As in commercial practice

*Training.*—Y trailing cordon. .

Table of characteristics:

*Plant*.—Time of vegetative bud burst: beginning of March.

*Young shoot*.—Openness of tip: closed. Density of prostrate hairs on tip: dense. Anthocyanin coloration of prostrate hairs on tip: very weak. Green color: green RHS 144 A. Green color of upper side of undeveloped leaf blade: medium green RHS 144 A with over color medium red brown between RHS 166 C and 166 D. Green color of lower side of undeveloped leaf blade: medium green RHS 144 A with over color medium red brown between RHS 166 C and 166 D. Anthocyanin coloration: medium.

*Young leaf*.—Density of hairs between main veins on lower side of blade: medium. Glossiness of upper side: strong. Glossiness of lower side: weak.

*Shoot*.—Length of internode: 8-11 cm. Thickness of internode: 5-7 mm. Color of dorsal side of internode: green RHS 144 B. Anthocyanin coloration of dorsal side of internode: weak to medium RHS 178 BC. Distribution of anthocyanin coloration of dorsal side of internode: striped. Color of ventral side of internode: light green RHS 144 B. Anthocyanin coloration of ventral side of internode: absent. Distribution of anthocyanin coloration of ventral side of internode: not relevant. Erect hairs on internodes: absent. Height of node: about 2 cm. Swelling at node: about 2 mm. Diameter of node: 11-16 mm. Color of dorsal side of node: green RHS 144 B. Anthocyanin coloration of dorsal side of node: weak to medium RHS 178 B. Distribution of anthocyanin coloration of dorsal side of node: striped. Color of ventral side of node: green RHS 144 B. Anthocyanin coloration of ventral side of node: absent. Distribution of anthocyanin coloration of ventral side of node: not relevant. Pubescence of node: absent Length of tendril: 16-27 cm. Diameter of tendril at base: 2-3 mm. Diameter of tendril at tip: 1-2 mm. Pubescence of tendril: absent. Number of bifurcations per tendril: 3-5. Color of tendril: light yellow green RHS 145 A. Anthocyanin coloration of tendril: weak to medium, at base brown red RHS 178 B. Consecutive tendrils: each node.

*Inflorescence*.—Length: 16-25 cm. Maximum diameter: 8-10 cm. No. of side branches: 13-15. Attitude of side branches: semi upright. Length of longest side branch: 5-6 cm. Thickness of main axis: About 4 mm. Green color of main axis: light green RHS 144 B. Anthocyanin coloration of main axis: weak. Pubescence of main axis: absent.

*Flower*.—Sexual organs: fully developed stamen and fully developed gynoecium.

*Pedicel*.—Length: 4-6 mm. Thickness: 1-2 mm. Green color: light green RHS 144 B. Pubescence: absent.

*Stamen*.—Number: five. Length of filament: 3-4 mm. Thickness of filament: minuscule. Pubescence of filament: absent. Surface: smooth. Color: light green RHS 145 C.

*Anther*.—Shape: transverse elliptic. Length: minuscule. Color: light green RHS 145 C.

*Pollen*.—Color: yellow RHS 150 B.

*Ovary*.—Shape: elliptic. Color: green RHS 144 A. Length: 2-3 mm. Diameter: 1-2 mm. Surface: smooth.

*Style*.—Length: minuscule.

*Stigma*.—Size: minuscule. Color: yellow RHS 150 B.

*Mature leaf*.—Blade length: 16-21 cm. Blade width: 17-20 cm. Shape of blade: pentagonal. Green color of upper side: dark green RHS 139 A. Green color of lower side: dark green RHS 137 B. Glossiness of upper side: medium. Glossiness of lower side: medium. Profile in cross section: undulated. Blistering of upper side: medium. Number of lobes: five. Central lobe length: about 11 cm. Central lobe width: about 9.5 cm. Upper, side lobe length: 7-9 cm. Upper, side lobe width: about 7 cm. Pubescence of veins on upper side: sparse. Pubescence of veins on lower side: medium. Green color of veins on upper side: green RHS 137 C. Green color of veins on lower side: yellow green RHS 145 A. Anthocyanin coloration of veins on upper side: absent. Anthocyanin coloration of veins on lower side: absent. Depth of upper lateral sinus: medium. Arrangement of lobes of upper leaf sinus: slightly overlapping. Arrangement of lobes of petiole sinus: open. Petiole sinus limited by veins: absent. Length of distal tooth: 10-16 mm. Width of distal tooth: 13-20 mm. Ratio length/width of distal tooth: small. Shape of tooth: straight on both sides. Anthocyanin coloration of main veins on upper side of blade: absent. Density of hairs between veins on upper side of blade: medium. Density of hairs between veins on lower side of blade: medium to strong. Length of petiole compared to main vein: similar. Length of petiole: 11-14 cm. Petiole thickness: 4-6 mm.

*Petiole*.—Green color of upper side: green yellow RHS 145 A. Anthocyanin coloration of upper side: absent. Green color of lower side: green yellow RHS 145 A. Anthocyanin coloration of lower side: weak. Pubescence: weak.

*Fruit*.—Time of beginning of berry ripening: N/R.

*Bunch*.—Size (peduncle excluded): N/R. Length (peduncle included): about 25 cm. Maximum diameter: 10-12 cm. Weight: about 300 gr. General shape: spindle. Peduncle length: 3-5 cm. Peduncle thickness: about 5 mm. Peduncle color: green RHS 144 B. Peduncle lignification: absent. Density: medium.

*Pedicel*.—Length: about 1 cm. Thickness: about 2 mm. Color: green RHS 144 B.

*Berry*.—Detachment: easy. Length: about 27 mm. Diameter: about 21 mm. Weight: about 6 gr. Shape in profile: elongated-elliptic. Shape in cross section: rounded. Depression at distal end: present. Color of skin (without bloom): yellowish green RHS 145 B. Amount of bloom: none. Surface: Smooth. Thickness of skin: medium. Adherance of skin to flesh: strong. Flesh color: light green RHS 145 C. Flesh anthocyanin coloration: absent. Firmness of flesh: soft. Juiciness of flesh: medium. Particular flavor: absent. Formation of seeds: absent.

*Woody shoot*.—Length of node: variable. Main color (without bloom): brown RHS 177 B. Surface: rough. Shape in cross section: ribbed. Diameter: about 9 mm. Lenticels: not visible.

Usage: Table grape.

Disease\pest resistance: No atypical resistance has been noted.

What is claimed is:

1. A new and distinct grapevine variety, referred to as 'GREEN ANGELS', as herein described and illustrated by the characteristics set forth above.

* * * * *

UNITED STATES PATENT AND TRADEMARK OFFICE

CERTIFICATE OF CORRECTION

PATENT NO. : PP23,199 P3
APPLICATION NO. : 12/929129
DATED : November 20, 2012
INVENTOR(S) : Avichai Perl et al.

It is certified that error appears in the above-identified patent and that said Letters Patent is hereby corrected as shown below:

On the Title Page:

Item (54) "GRAPEVINE NAMED 'GREEN ONYX'" should be changed to:

(54) --GRAPEVINE NAMED 'GREEN ANGELS'--

Item (50) "Latin Name: *Vitis vinifera* L.
Varietal Denomination: GREEN ONYX" should be changed to:

(50) --Latin Name: *Vitis vinifera* L.
Varietal Denomination: GREEN ANGELS--

Signed and Sealed this
Twenty-ninth Day of January, 2013

David J. Kappos

David J. Kappos
*Director of the United States Patent and Trademark Office*